United States Patent
Golz-Berner et al.

(10) Patent No.: US 7,459,166 B2
(45) Date of Patent: Dec. 2, 2008

(54) COSMETIC PRODUCT CONTAINING MINERAL WATER FOR REMINERALIZING AND REJUVENATING THE SKIN

(75) Inventors: Karin Golz-Berner, Monaco (MC); Leonhard Zastrow, Monaco (MC); Dorothée Bernini Sichling, Monaco (MC)

(73) Assignee: Coty B.V. (NL)

( * ) Notice: Subject to any disclaimer, the term of this patent is extended or adjusted under 35 U.S.C. 154(b) by 215 days.

(21) Appl. No.: 10/555,489

(22) PCT Filed: May 21, 2004

(86) PCT No.: PCT/EP2004/005543

§ 371 (c)(1),
(2), (4) Date: Nov. 3, 2005

(87) PCT Pub. No.: WO2004/105717

PCT Pub. Date: Dec. 9, 2004

(65) Prior Publication Data

US 2007/0086966 A1    Apr. 19, 2007

(30) Foreign Application Priority Data

May 28, 2003 (DE) ................................ 103 25 158

(51) Int. Cl.
*A61K 8/02* (2006.01)
*A61K 36/00* (2006.01)
*A61K 33/00* (2006.01)

(52) U.S. Cl. .................... 424/401; 424/600; 424/725
(58) Field of Classification Search ............... None
See application file for complete search history.

(56) References Cited

U.S. PATENT DOCUMENTS

| | | | |
|---|---|---|---|
| 5,445,824 A * | 8/1995 | Someya | 424/520 |
| 5,614,215 A | 3/1997 | Simonnet et al. | |
| 5,690,946 A | 11/1997 | Gagnebien et al. | |
| 6,190,678 B1 * | 2/2001 | Hasenoehrl et al. | 424/401 |
| 6,426,080 B1 | 7/2002 | Golz-Berner et al. | |
| 2004/0115163 A1 * | 6/2004 | Gedouin et al. | 424/74 |

FOREIGN PATENT DOCUMENTS

| | | |
|---|---|---|
| DE | 101 40 538 A1 | 3/2003 |
| EP | 1 170 002 A1 | 1/2002 |
| FR | 2 802 413 A1 | 12/1999 |
| FR | 2 819 718 A1 | 1/2001 |

OTHER PUBLICATIONS

Linter K. et al., "Biologically Active Peptides: From a Laboratory Bench Curiosity to a Functional Skin Care Product," Int. J. Cosm. Sci., vol. 22, pp. 207-218 (2000).

* cited by examiner

*Primary Examiner*—Patricia Leith
(74) *Attorney, Agent, or Firm*—Akerman Senterfitt; Gregory A. Nelson; Gregory M. Lefkowitz

(57) ABSTRACT

A cosmetic composition that can be used to remineralize human skin and to counteract the effects of ageing of skin. The composition contains 0.5-3% water of volcanic origin containing 0.01-0.05 mg/L Fe, 100-300 mg/L K, 1,000-2,000 mg/L Na, 80-200 mg/L Mg, 50-150 mg/L Ca, 50-150 mg/L Si, 0.01 -0.1 mg/L P, 0.001-0.005 mg/L Se and 0.01-0.03 mg/L Zn. In addition, the composition optionally contains 0.2-0.8% of an extract from samphire *Crithmum maritimum*, 0.3-0.9% of the peptide palmitoyl-gly-his-lys and 0.8-1.25% hydrolysed soy protein.

14 Claims, No Drawings

COSMETIC PRODUCT CONTAINING MINERAL WATER FOR REMINERALIZING AND REJUVENATING THE SKIN

CROSS REFERENCE TO RELATED APPLICATION

This application is a national stage of PCT/EP2004/005543 filed May 21, 2004 and based upon DE 103 25 158.8 filed May 28, 2003 under the International Convention.

BACKGROUND OF THE INVENTION

1. Field of the Invention

The invention relates to a cosmetic composition that can be used to remineralise human skin and to counteract the effects of ageing on the latter.

2. Related Art of the Invention

The use of mineral waters for cosmetic purposes is known. In EP 699432 B1, a cosmetic composition is claimed which contains at least one active agent having an irritant effect, such as salicylic acid, α-hydroxy acids, retinoids or benzoyl peroxide, and at least one soothing agent selected from among thermal waters or mineral waters having a mineral content of at least 700 mg/l and a total concentration of carbonate and hydrogen carbonate of at least 360 mg/l.

In addition, EP 1170002 describes a method for reducing the loss of skin elasticity, which includes the use of mineral water containing at least 200 mg/l minerals, thereof 30-150 mg/l Ca and 10-50 mg/l Mg.

SUMMARY OF THE INVENTION

The object of the invention is to provide a cosmetic having long-lasting remineralising properties. Another object is to supplement the remineralising effect with a rejuvenating and anti-ageing effect.

DETAILED DESCRIPTION OF THE INVENTION

According to the invention, the cosmetic for remineralising and rejuvenating the skin is characterised in that, in addition to cosmetic auxiliaries or carriers and further active agents, it contains 0.5 to 3% by weight water of volcanic origin containing 0.01-0.05 mg/l iron
100-300 mg/l potassium
1,000-2,000 mg/l sodium
80-200 mg/l magnesium
50-150 mg/l calcium
50-150 mg/l silicon (as $SiO_2$)
0.01-0.1 mg/l phosphorus
0.001-0.005 mg/l selenium
0.01-0.03 mg/l zinc.

The use of volcanic water from overground volcanic lakes brings about a noticeable re-sensitisation of the skin, which loses up to 50% of its sensitivity during the ageing process between 50 and 65 years of age. In this way, the skin's barrier function in the epidermis, especially in the stratum corneum, is improved. It is particularly important that the stratum corneum be moisturised since this determines the elasticity and plasticity, i.e. mechanical properties, of the skin. In the stratum corneum, water is present in two thermodynamic forms: as free water in which various ions or molecules are dissolved, and as bound water which interacts with the lipids and proteins of the stratum corneum. The bound water makes up 20-30% of the total volume. In dry skin, free water is lost, which is transported from the dermis to the skin surface via the basal layer, and in addition the amount of water that is bound to the enzyme responsible for corneodesmosome degradation is reduced. As a consequence, the skin's plasticity and elasticity will decrease.

Furthermore, the delicate balance of hygroscopic substances in the stratum corneum, which are known as NMF (Natural Moisturising Factors) and include a number of ions such as Na, K, Ca, Cl, phosphorus and certain organic acids such as urea and amino acids, will be upset.

It has been found that volcanic water is rich in various minerals whose form and composition are suited to the skin's susceptibility and is therefore particularly suitable for contributing to the long-lasting remineralisation of the skin. The mineral ions dissolved out of mineral rock over long periods of time, such as iron, selenium, zinc, calcium, magnesium, sodium, potassium and phosphorus, act as cofactors in the enzymatic biochemical reactions, contributing to coming closer to the skin's natural structure as regards the composition of said ions even for older skin. This applies to both the Na and K contents, which are important for controlling the water content, and the Ca, Mg and P contents, which play decisive roles in the ageing and growth processes of the cells.

The inventive composition containing a water which, in contrast to known thermal and mineral waters, contains only very small amounts of carbonate and hydrogen carbonate, i.e. below 1-2 mg/l in total, and which contains very large amounts of Na, Mg and Si and at the same time skin-adequate concentrations of P, Se and Zn shows unexpectedly high values in elasticity measurements using known methods (cutometer), even after longer periods of time.

It is preferred that water from a volcanic lake in the region of Clermont-Ferrand (France) be used.

In a second embodiment of the invention, the cosmetic contains 0.01 to 2% by weight of an extract from samphire Crithmum maritimum as an additional active agent. It has been found that samphire extract significantly influences the synthesis of ceramides and that e.g. a concentration of 1% improves ceramide synthesis by approx. 70%.

In a third embodiment of the invention, the cosmetic contains 0.01 to 2% by weight of a solution of the peptide palmitoyl-gly-his-lys in propylene glycol as an additional active agent, preferably in combination with 0.01 to 2% by weight of an extract from samphire Crithmum maritimum. In this way, the collagen synthesis by the fibroblasts is stimulated, as is the synthesis of hyaluronic acid. The peptide is dissolved in propylene glycol in a concentration of approx. 100 mg/l (or 0.001 to 0.2% of peptide).

In a fourth embodiment of the invention, the cosmetic contains 0.01 to 5% by weight hydrolysed soy protein as an additional active agent, preferably in combination with 0.01 to 2% by weight of an extract from samphire Crithmum maritimum and 0.01 to 2% by weight of the peptide palmitoyl-gly-his-lys. In this combination, the cosmetic shows a moisturising effect lasting for several hours without the addition of usual moisturisers, and at the same time a reduction of small skin wrinkles by approx. 35% even after 8 hours.

In a fifth embodiment of the invention, the cosmetic contains a mixture of plant extracts with an alcoholic base as an additional active agent, consisting of 0.2% by weight of an extract from green coffee beans, 0.2% by weight of an extract from the leaves of Camellia sinensis, 0.2% by weight of an extract from Ponagamia pinnata and 0.2% by weight of an extract from the roots of Angelica archangelica and 99.2% by weight ethanol. The aforesaid mixture, whose active agents are not encapsulated in liposomes, can make up 0.1 to 2% by weight of the cosmetic relative to the cosmetic's total weight.

It has been found that such an active mixture has an unexpectedly high radical protection factor (RPF) of approx. 1,800 radicals per mg, determined by measuring the number of free radicals in a solution of a test substance ($S_1$) by means of electron spin resonance (ESR), compared to the ESR measuring result of the cosmetic active preparation according to the equation $$RPF=(RC \times RF)/PI$$

wherein $RF=(S_1-S_2)/S_1$; RC=concentration of the test substance (radicals/ml); PI=concentration of the active preparation (mg/ml) (measurement according to WO 99/66881).

The inventive cosmetic further contains certain cosmetic auxiliaries and carriers as they are commonly used in such preparations, e.g. water, preservatives, colourants, pigments having a colouring effect, thickeners, fragrances, alcohols, polyols, esters, electrolytes, gel-forming agents, silicone oils, polymers, copolymers, emulsifiers, stabilisers.

Further cosmetic active agents which can also be contained include e.g. inorganic and organic sunscreens, moisturisers, enzymes and other plant-based active agents.

As used herein, SIMULGEL NS® is used to describe a thickening and emulsifying agent comprising a hydroxyethyl acrylate and sodium acryloyldimethyltaurate copolymer, squalane and polysorbate 60.

Particularly preferred cosmetic compositions are those provided in the form of a moisturising skin balm containing 0.08 to 1.4% by weight water of volcanic origin, 0.2 to 0.8% by weight of an extract from samphire *Crithmum maritimum*, 0.3 to 0.9% by weight of the peptide palmitoyl-gly-his-lys and 0.8 to 1.25% by weight hydrolysed soy protein, and which in addition contains 1-4% by weight glycerine, 1-5% by weight butylene glycol or propylene glycol, 2-4% by weight cetearyl alcohol, 6-9% by weight dicapryl carbonate, 0.5-1.3% by weight phenoxyethanol, 0.1-0.5% by weight chlorphenesin, 2.5-4% by weight Beheneth-25, 6-9% by weight shea butter, 2-4% by weight modified maize starch powder, 2.5-4% by weight SIMULGEL NS®, 1-3.5% by weight dimethicone, 0.05-0.5% by weight colourants, 0.05-0.2% by weight organic sunscreens for the colourants, 0.1-0.5% by weight preservative, 0.05-0.2% by weight tetrasodium ethylenediamine tetraacetic acid and 0.1-0.5% by weight of a mixture of alcoholic extracts from plants consisting of 0.2% by weight seeds of green coffee beans, 0.2% by weight *Camellia sinensis* leaves, 0.2% by weight *Ponagamia pinnata*, 0.2% by weight *angelica* root and 99.2% by weight ethanol. The remainder up to 100% by weight is distilled water.

Further particularly preferred cosmetic compositions are those provided in the form of a highly moisturising gel for normal and oily skin, containing 0.08 to 1.4% by weight water of volcanic origin, 0.2 to 0.8% by weight of an extract from samphire *Crithmum maritimum*, 0.3 to 0.9% by weight of the peptide palmitoyl-gly-his-lys and 0.8 to 1.25% by weight hydrolysed soy protein, and which in addition contains 10-14% by weight cyclo-methicone, 0.5-2% by weight phenyl trimethicone, 1-5% by weight butylene glycol or propylene glycol, 3-5% by weight ethanol, 0.1-0.5% by weight chlorphenesin, 2-4% by weight powdered methyl methacrylate crosspolymer, 2.5-4% by weight SIMULGEL NS®, 1-3.5% by weight dimethicone, 0.05-0.5% by weight colourants, 0.1-0.5% by weight preservative, 0.1-0.5% of the mixture of alcoholic extracts from plants mentioned above, 0.1-0.5% by weight perfume, distilled water making up the remainder up to 100% by weight.

The invention will hereinafter be explained in more detail by means of examples. All quantities are in % by weight unless indicated otherwise.

EXAMPLE 1

Moisturising skin balm

| Phase A | |
| --- | --- |
| Water | q.s. ad 100 |
| Glycerine | 2.0 |
| Butylene Glycol | 2.0 |
| Tetrasodium Ethylenediamine Tetra-acetic Acid | 0.1 |
| Preservative | 0.4 |
| pH adjuster | 0.3 |
| Phase B | |
| Beheneth-25 | 3.3 |
| Cetearyl Alcohol | 2.7 |
| Dicapryl Carbonate | 8.5 |
| Shea Butter | 7.2 |
| Phenoxyethanol | 0.9 |
| Modified maize starch powder | 3.0 |
| Dimethicone | 1.4 |
| SIMULGEL NS ® (a thickening and emulsifying agent comprising hydroxyethyl acrylate and sodium acryloyldimethyltaurate copolymer, squalane and polysorbate (60) | 3.5 |
| Phase C | |
| Colourants | 0.1 |
| Water of volcanic origin | 1.0 |
| Peptide palmitoyl-gly-his-lys | 0.5 |
| Mixture of alcoholic extracts from plants* | 0.2 |
| Crithmum maritimum extract | 0.5 |
| Hydrolysed soy protein | 1.0 |
| Benzophenone-4 (for colourants) | 0.4 |

*Consisting of 0.2% by weight seeds of coffee beans, 0.2% by weight Camellia sinensis leaves, 0.2% by weight Ponagamia pinnata, 0.2% by weight angelica root and 99.2% by weight ethanol.

EXAMPLE 2

Moisturising gel

| Phase A | |
| --- | --- |
| Water | q.s. ad 100 |
| SIMULGEL NS ® (a thickening and emulsifying agent comprising hydroxyethyl acrylate and sodium acryloyldimethyltaurate copolymer, squalane and polysorbate 60) | 3.2 |
| Propylene Glycol | 4.0 |
| pH adjuster | 0.3 |
| Methyl Methacrylate Crosspolymer | 1.2 |
| Phase B | |
| Cyclomethicone | 11.5 |
| Dimethicone | 3.0 |
| Phenyl Trimethicone | 1.0 |
| Peptide palmitoyl-gly-his-lys | 0.5 |

-continued

| Phase C | |
|---|---|
| Ethanol | 4.0 |
| Phase D | |
| Colourants | 0.3 |
| Perfume | 0.2 |
| Preservative | 0.3 |
| Water of volcanic origin | 1.0 |
| Mixture of alcoholic extracts from plants* | 0.2 |
| Crithmum maritimum extract | 0.5 |
| Hydrolysed soy protein | 1.0 |

*Consisting of 0.2% by weight seeds of coffee beans, 0.2% by weight Camellia sinensis leaves, 0.2% by weight Ponagamia pinnata, 0.2% by weight angelica root and 99.2% by weight ethanol.

Phases A and B are mixed separately at approx. 60° C., Phases C and D are mixed at approx. 35° C., and all four phases are combined with one another while stirring at approx. 35° C.

EXAMPLE 3

Elasticity Measurements

The skin's viscoelasticity was measured using a Cutometer SEM 575® (Courage+Khazaka, Cologne, Germany) and applying a suction pressure of 500 mbar. A skin area measuring 2 mm in diameter was sucked up at a constant suction pressure for 10 seconds and then released from pressure while measuring the penetration depth of the skin. The $U_v/U_e$ ratio (viscoelastic recovery following elastic deformation/elastic deformation of the skin during application of the vacuum) was determined.

The measurements were carried out on the calves of a group of 18 test persons, performing one measurement per day over a period of 3 weeks after the test persons had been acclimatised to 22° C. ±2.5° C. and 30% relative air humidity for 20 minutes.

The balm according to Example 1 (Sample A), which was applied to a calf twice a day, showed an increase of the $U_v/U_e$ ratio by 10% after 3 days, by 18% after 6 days and by 22% after 14 days, compared to a balm according to Example 1, yet without Phase C (Sample B), which was also applied twice per day. After 3 weeks, the curve of Sample A resembled an asymptote, while the curve of Sample B fell. This means, the values of Sample A were 25% higher than those of Sample B after 3 weeks, which clearly demonstrates the long-lasting effect of the inventive additives.

We claim:

1. A skin balm for remineralising and rejuvenating the skin which comprises 0.08 to 1.4% by weight water of volcanic origin, 0.01 to 2% by weight of an extract from samphire *Crithmum maritimum*, 0.01 to 2% by weight of the peptide palmitoyl-gly-his-lys and 0.01 to 5% by weight hydrolysed soy protein, and further comprises:
   a) 1-4% by weight glycerine,
   b) 1-5% by weight butylene glycol or propylene glycol,
   c) 2-4% by weight cetearyl alcohol,
   d) 6-9% by weight dicapryl carbonate,
   e) 0.5-1.3% by weight phenoxyethanol,
   f) 0.1-0.5% by weight chloiphenesin,
   g) 2.5-4% by weight Beheneth-25,
   h) 6-9% by weight shea butter,
   i) 2-4% by weight modified maize starch powder,
   j) 2.5-4% by weight a thickening and emulsifying agent comprising a hydroxyethyl acrylate and sodium acryloyldimethyltaurate copolymer, squalane and polysorbate 60,
   k) 1-3.5% by weight dimethicone,
   l) 0.05-0.5% by weight colourants,
   m) 0.05-0.2% by weight organic sunscreens for the colourants,
   n) 0.1-0.5% by weight preservative,
   o) 0.1-0.5% by weight of a mixture comprising alcoholic extracts from plants consisting of 0.2% by weight coffee seeds,
      0.2% by weight *Camellia sinensis* leaves,
      0.2% by weight *Ponagamia pinnata* and
      0.2% by weight *angelica* root; and
      99.2% by weight ethanol,
   p) 0.05-0.2% by weight tetrasodium ethylenediamine tetraacetic acid, and
   q) remainder up to 100% by weight distilled water, wherein said water of volcanic origin comprises below 1-2 mg/L carbonate ($CO_3$),
   below 1-2 mg/L hydrogen carbonate ($HCO_3$),
   0.01-0.05 mg/L iron,
   100-300 mg/L potassium,
   1,000-2,000 mg/L sodium,
   80-200 mg/L magnesium,
   50-150 mg/L calcium,
   50-150 mg/L silicon (as $SiO_2$),
   0.01-0.1 mg/L phosphorus,
   0.001-0.005 mg/L selenium and
   0.01-0.03 mg/L zinc.

2. The skin balm according to claim 1, wherein said water of volcanic origin is surface water from a volcanic lake.

3. The skin balm according to claim 1 wherein said water of volcanic origin contains:
   0.025-0.05 mg/L iron,
   170-300 mg/L potassium,
   1,600-2,000 mg/L sodium,
   130-200 mg/L magnesium,
   90-150 mg/L calcium,
   90-150 mg/L silicon (as $SiO_2$),
   0.06-0.1 mg/L phosphorus,
   0.003-0.005 mg/L selenium and
   0.02-0.03 mg/L zinc.

4. The skin balm of claim 1, comprising 0.2 to 0.8% by weight of an extract from samphire *Crithmum maritimum*.

5. The skin balm of claim 1, comprising 0.3 to 0.9% by weight of the peptide palmitoyl-gly-his-lys.

6. The skin balm of claim 1, comprising 0.8 to 1.25% by weight hydrolysed soy protein.

7. The skin balm of claim 1, comprising 0.2 to 0.8% by weight of an extract from samphire *Crithmum maritimum*, 0.3 to 0.9% by weight of the peptide palmitoyl-gly-his-lys, and 0.8 to 1.25% by weight hydrolysed soy protein.

8. A cosmetic gel for remineralising and rejuvenating the skin which comprises 0.08 to 1.4% by weight water of volcanic origin, 0.01 to 2% by weight of an extract from samphire *Crithmum maritimum*, 0.01 to 2% by weight of the peptide palmitoyl gly-his-lys and 0.01 to 5% by weight hydrolysed soy protein, and further contains:
   a) 10-14% by weight cyclomethicone,
   b) 0.5-2% by weight phenyl trimethicone,
   c) 1-5% by weight butylene glycol or propylene glycol,
   d) 3-5% by weight ethanol,
   e) 0.1-0.5% by weight chlorphenesin,
   f) 2-4% by weight powdered methyl methacrylate crosspolymer, g) 2.5-4% by weight a thickening and emulsifying agent comprising a hydroxyethyl acrylate and sodium acryloyldimethyltaurate copolymer, squalane and polysorbate 60,
h) 1-3.5% by weight dimethicone,
i) 0.05-0.5% by weight colourants,
j) 0.1-0.5% by weight preservative,
k) 0.1-0.5% by weight of a mixture comprising alcoholic extracts from plants consisting of 0.2% by weight coffee seeds,
0.2% by weight *Camellia sinensis* leaves,
0.2% by weight *Ponagamia pinnata* and
0.2% by weight *angelica* root;
and 99.2% by weight ethanol,
l) 0.1-0.5% by weight perfume, and
m) remainder up to 100% by weight distilled water, wherein said water of volcanic origin comprises:
below 1-2 mg/L carbonate ($CO_3$),
below 1-2 mg/L hydrogen carbonate ($HCO_3$),
0.01 -0.05 mg/L iron,
100-300 mg/L potassium,
1,000-2,000 mg/L sodium,
80-200 mg/L magnesium,
50-150 mg/L calcium,
50-150 mg/L silicon (as $SiO_2$),
0.01 -0.1 mg/L phosphorus,
0.001-0.005 mg/L selenium, and
0.01 -0.03 mg/L zinc.

9. The cosmetic gel of claim 8, comprising 0.2 to 0.8% by weight of an extract from samphire *Crithmum maritimum*.

10. The cosmetic gel of claim 8, comprising 0.3 to 0.9% by weight of the peptide palmitoyl-gly-his-lys.

11. The cosmetic gel of claim 8, comprising 0.8 to 1.25% by weight hydrolysed soy protein.

12. The cosmetic gel of claim 8, comprising 0.2 to 0.8% by weight of an extract from samphire *Crithmum maritimum*, 0.3 to 0.9% by weight of the peptide palmitoyl-gly-his-lys, and 0.8 to 1.25% by weight hydrolysed soy protein.

13. The cosmetic gel according to claim 8, wherein said water of volcanic origin is surface water from a volcanic lake.

14. The cosmetic gel according to claim 8, wherein said cosmetic contains water of volcanic origin containing
0.025-0.05 mg/L iron
170-300 mg/L potassium
1,600-2,000 mg/L sodium
130-200 mg/L magnesium
90-150 mg/L calcium
90-150 mg/L silicon (as $SiO_2$)
0.06-0.1 mg/L phosphorus
0.003-0.005 mg/L selenium
0.02-0.03 mg/L zinc.

* * * * *